(12) United States Patent
Pierre et al.

(10) Patent No.: US 10,794,855 B2
(45) Date of Patent: Oct. 6, 2020

(54) HIGH SENSITIVITY ION SELECTIVE SENSORS IMPLEMENTED THROUGH FEEDBACK CIRCUITRY

(71) Applicant: Palo Alto Research Center Incorporated, Palo Alto, CA (US)

(72) Inventors: Adrien Pierre, South San Francisco, CA (US); Sean Emerson Doris, San Francisco, CA (US); Robert A. Street, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 244 days.

(21) Appl. No.: 16/117,593

(22) Filed: Aug. 30, 2018

(65) Prior Publication Data
US 2020/0072786 A1 Mar. 5, 2020

(51) Int. Cl.
*G01N 27/414* (2006.01)
*H03F 3/45* (2006.01)
*G01N 33/50* (2006.01)

(52) U.S. Cl.
CPC ..... *G01N 27/4145* (2013.01); *H03F 3/45475* (2013.01); *G01N 33/50* (2013.01); *H03F 2200/129* (2013.01); *H03F 2203/45116* (2013.01)

(58) Field of Classification Search
None
See application file for complete search history.

(56) References Cited

U.S. PATENT DOCUMENTS

2008/0128687 A1 6/2008 Armgarth et al.

OTHER PUBLICATIONS

R. Shiwaku, et al. "A printed organic amplification system for wearable potentiometric electrochemical sensors" Scientific Reports, 8 (1): p. 1-8, Mar. 2018.*
Gross, E. M., Kelly, R. S. & Cannon, D. M. J. No Title. Analytical Electrochemistry: Potentiometry Available at: https://www2.chemistry.msu.edu/courses/cem837/ISE.doc.pdf (available prior to Aug. 30, 2018).
Khodagholy, D. et al High transconductance organic electrochemical transistors. 4, 2133 (2013).
Sessolo, M. Rivnay, J., Bandiello, E., Malliaras, G. G. & Bolink, H. J. Ion-Selective Organic Electrochemical Transistors. Adv. Mater. 26, 4803-4807 (2014).

* cited by examiner

*Primary Examiner* — J. Christopher Ball
(74) *Attorney, Agent, or Firm* — Fay Sharpe LLP (57) ABSTRACT

The following relates generally to ion sensing using organic electrochemical transistors (OECTs). In one aspect, a device comprises: an amplification portion including an OECT; a feedback portion that receives a differential voltage from the amplification portion and outputs a feedback signal; and a readout portion which receives the feedback signal and outputs an output voltage.

16 Claims, 9 Drawing Sheets

FIG. 4

HIGH SENSITIVITY ION SELECTIVE SENSORS IMPLEMENTED THROUGH FEEDBACK CIRCUITRY

BACKGROUND

The present application relates generally to ion sensing using organic electrochemical transistors (OECTs).

Figure 1A:
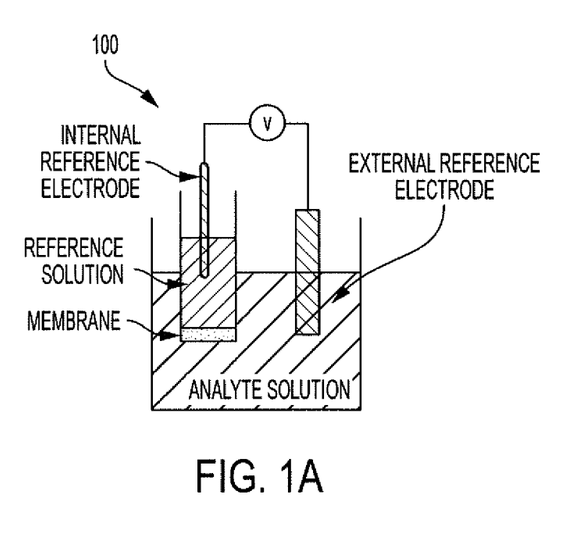
FIG. 1A shows the setup for a conventional ISM system 100.
Figure 1B:
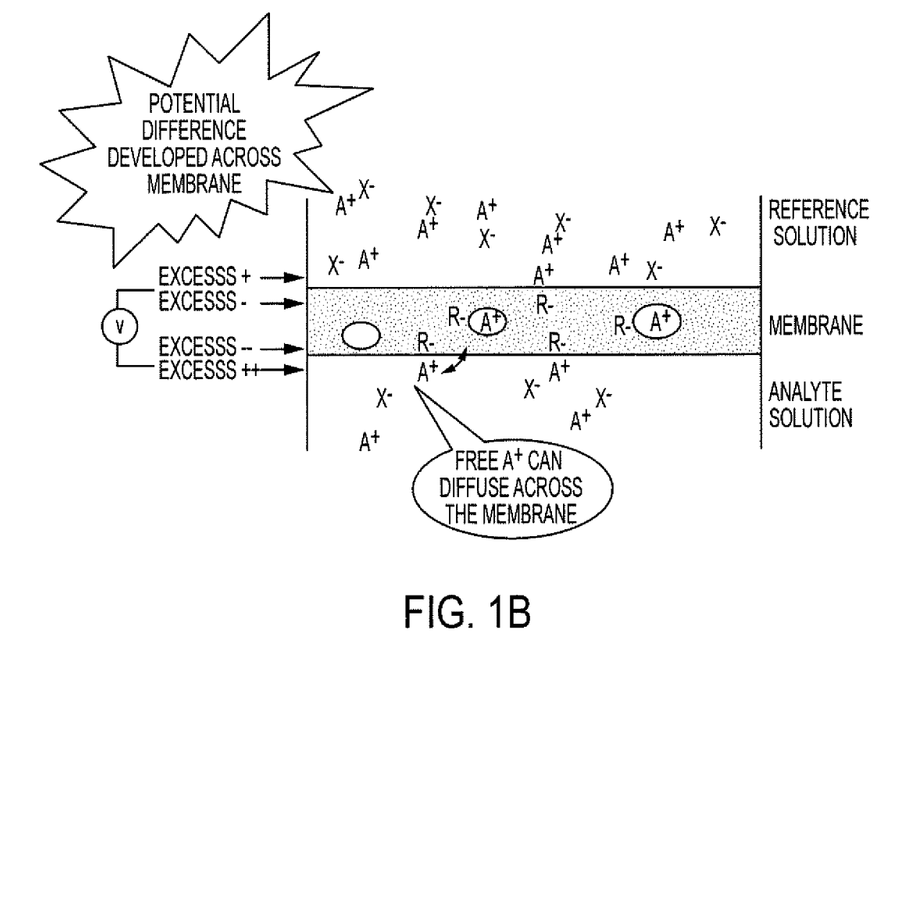
FIG. 1B shows an interface of a membrane and an electrolyte.

Ion sensing in aqueous solutions is an extremely useful tool for analyzing biological fluids, environmental contamination and process purity control. Not only is it desirable for ion sensing electrodes to have high sensitivity and a wide dynamic range, but also to have great selectivity for specific ions. This is typically implemented through the use of plastic-based ion-selective membranes (ISMs), which show good sensitivity and are relatively inexpensive compared to other types of ion-selective electrodes. FIG. 1A shows the setup for a conventional ISM system 100. An internal reference electrode, typically Ag/AgCl, is placed inside of a reference solution of known ion concentration. The ISM separates the reference solution from the analyte, the unknown solution, which is in contact with an external reference electrode. Ion exchange occurs at the interface of the membrane and the electrolyte as shown in FIG. 1B, leading to a voltage drop across the interface. The ionophore is designed with such a structure to only let a specific ion move into the membrane to perform this ion exchange. The amount of ion exchange is dependent on the ion concentration, resulting in a net voltage drop across the membrane that is read out by the difference between the internal and external reference electrodes.

BRIEF DESCRIPTION

In accordance with one aspect of the present application, a device for measuring ion concentration in an analyte solution includes an amplification portion comprising a first inverter and a second inverter, the first inverter comprising an ion sensing organic electrochemical transistor (OECT). The device may further include a feedback portion configured to: receive a voltage input from the OECT; and provide a feedback signal to the first inverter and a readout portion.

In the apparatus as described in the preceding paragraph, the first inverter may further comprise a non-sensing OECT comprising an encapsulant; and the second inverter may further comprise two non-sensing OECTs including encapsulants. The feedback portion may further comprise a comparator, a resistor, and a capacitor. The comparator may be configured to: receive the voltage input from the OECT at a positive input terminal of the comparator; and output a feedback voltage to the capacitor and the resistor. The capacitor may be connected to a negative input terminal of the comparator; and the resistor may be connected to the first inverter and the readout portion. In some embodiments, the resistor has a resistance of approximately 10 MΩ; and the capacitor has a capacitance of approximately 100 nF. In some implementations, the negative input terminal of the comparator is further connected to the second inverter. In some embodiments, the readout portion is configured to: receive the feedback signal at a positive input terminal of a comparator; and output an output voltage to a negative input terminal of the comparator.

In another aspect, there is a device for measuring ion concentration in an analyte solution, comprising: an amplification portion comprising a first inverter and a second inverter, the first inverter comprising an ion sensing organic electrochemical transistor (OECT). The feedback portion may be configured to: receive a differential voltage signal from the amplification portion; and provide a feedback signal to the first inverter and a readout portion.

In the apparatus as described in the preceding paragraph, the first inverter may further comprise a non-sensing OECT comprising an encapsulant; and the second inverter may comprise two non-sensing OECTs including encapsulants. The feedback portion may comprise a comparator, a resistor, and a capacitor. In some embodiments, the comparator is configured to: receive the differential voltage from the amplification portion; and output a feedback voltage to the capacitor and the resistor. In some implementations, the capacitor is connected to a negative input terminal of the comparator; and the resistor is connected to the first inverter and the readout portion. The negative input terminal of the comparator may further be connected to the second inverter. In some implementations, the first inverter may further comprise a non-sensing OECT comprising an encapsulant encapsulating a reference solution; and the second inverter may comprise two non-sensing OECTs including encapsulants encapsulating the reference solution.

In another aspect, there is a method of measuring ion concentration in an analyte solution, comprising: with an amplification portion comprising an ion sensing organic electrochemical transistor (OECT), outputting a differential voltage to a feedback portion; and with the feedback portion, providing a feedback signal to the amplification portion and a readout portion.

DETAILED DESCRIPTION

Organic electrochemical transistors (OECTs) integrated with ion-selective membranes (ISMs) enable transistors with ionic concentration-dependent channel conductance. Embodiments described herein propose the use of these devices in analog circuit configurations implementing feedback in order to create highly sensitive and precise ion-concentration sensing circuits. Initial simulations based on measured device performance demonstrate these circuits amplify the responsivity of standard capacitive ISMs, 60 mV/decade ion concentration, to 200 mV/decade.

In one aspect, the maximum responsivity of an OECT device is 60 mV/decade of ion concentration for monovalent ions ($Na^+$, $K^+$) and 30 mV/decade for divalent ions ($Ca^{2+}$, $Mg^{2+}$). This necessitates the use of high-precision analog-to-digital converters (ADCs) to give a precise readout if the concentration range of interest for a particular application is less than an order of magnitude.

Figure 2A:
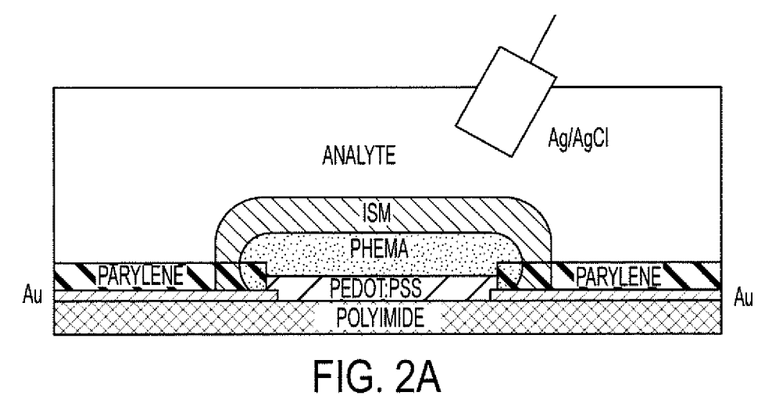
FIG. 2A shows an example of an organic electrochemical transistor (OECT).
Figure 2B:
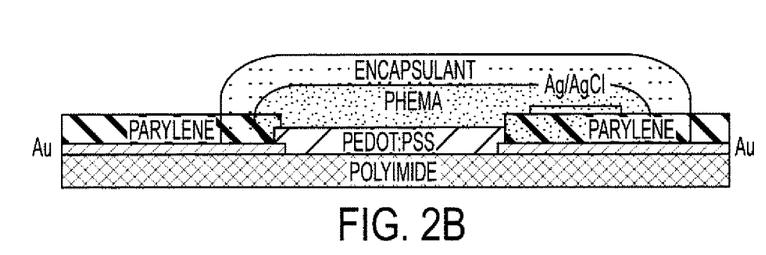
FIG. 2B shows a non-sensing OECT used for signal conditioning.

To further explain, OECTs are three terminal devices, with a source and drain connected together through a conductive polymer immersed in an electrolyte and a gate electrode in that same electrolyte acting as an electrochemical reference electrode to modulate the electrical conductivity of the channel. These are solution-processable devices, which allows for facile integration of ISMs between the gate electrode and channel to serve as a transconductance amplifier as shown in FIG. 2A. FIG. 2B shows a non-sensing OECT used for signal conditioning. The process of fabrication OECTs on polyimide substrates using gold source-drain electrodes with a PEDOT:PSS channel defined through a sacrificial parylene mask has already been reported in prior art. Ion-selective OECTs have also been shown in prior art using this same device architecture. PHEMA, poly(2-hydroxyethyl methacrylate), is a hydrogel that is stencil printed on top of the channel to hold the internal reference solution. After the PHEMA is dried and immediately before stencil printing the ISM, the device is soaked in the internal reference solution for the PHEMA to absorb. Subsequently printing the ISM not only makes the device ion-selective but also encapsulates the internal reference solution. This ion-selectively-gated transistor can then be configured with other non-sensing OECTs, pictured in FIG. 2C, to amplify the signal. These non-sensing devices are similar to the ion-sensing OECTs, except that the ISM is replaced with an encapsulant and the reference electrode is moved to contact with the PHEMA layer directly in order to modulate the channel without influence of external analyte.

In order to improve the responsivity of ion sensors, the systems and methods described herein propose the use of OECTs integrated in a negative feedback amplification scheme to increase the sensitivity of ion detection.

Figure 2C:
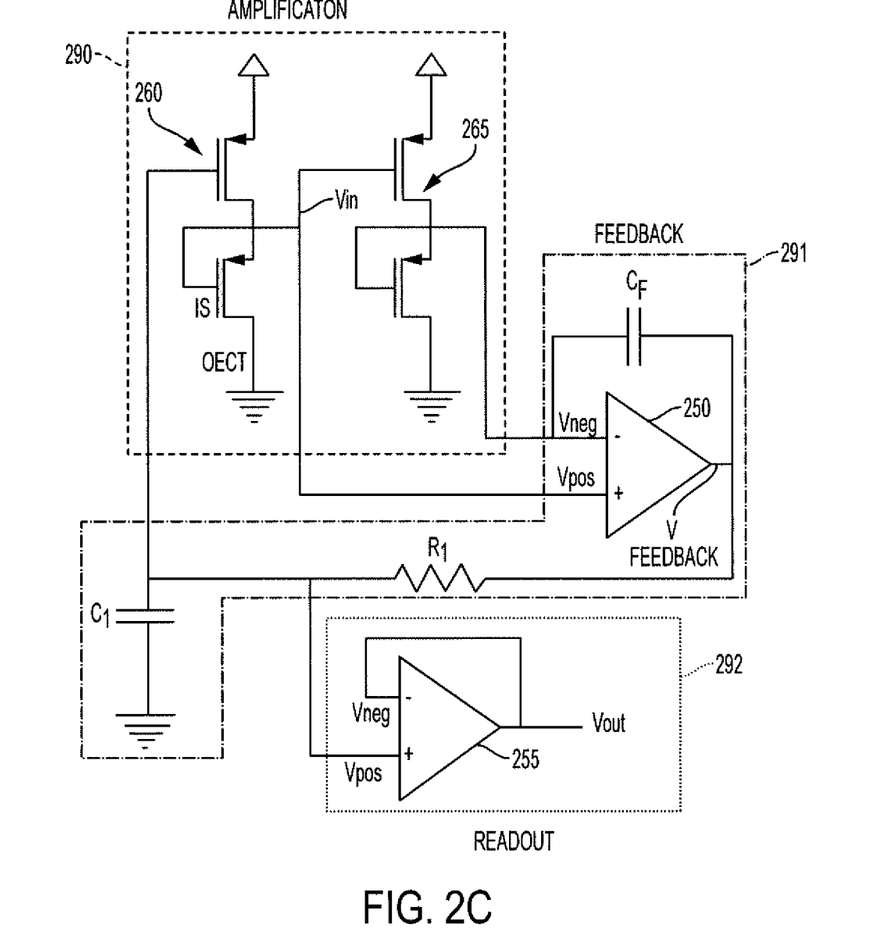
FIG. 2C shows an embodiment of a system described herein.

FIG. 2C shows the embodiment of this system. The first stage (amplification portion 290) serves to amplify the ion-selective OECT signal. This is achieved through two inverters 260, 265 connected in series with one ion-selective pull up transistor acting as the input, $V_{in}$, which is connected to a feedback portion 291. The output of the amplification portion 290 is a differential signal that is fed into a comparator 250 of the feedback portion 291. The comparator 250 outputs back to $V_{in}$ in a negative feedback configuration to provide stability to the system. The large resistor $R_1$ and capacitor $C_1$ (e.g., 10 MΩ and 100 nF, respectively) dampen the response to prevent oscillating. In some embodiments, a 1 nF capacitor $C_F$ is used as the feedback loop of the comparator 250 to prevent high frequency oscillations. A voltage buffer is used to readout the signal $V_{in}$ since the high impedance of the RC network in the feedback loop is high and can be easily loaded by the low input impedance of ADCs (~100 kΩ).

The device operates in steady state at the point where the differential output from the amplification portion 290 is 0 V, i.e. both inverters 260, 265 output the same voltage. A perturbation in the conductance of the ion-selective OECT, say a decrease in resistance, will cause a rise in the output of the first inverter 260 and a decrease in output of the second inverter 265, which correspondingly feed into the non-inverting and inverting terminals of the comparator 250. This input causes the comparator 250 to output a high voltage (limited by the supply voltage) $V_{feedback}$, which is dampened by the large RC time constant and feeds back to the input of amplification portion 290, $V_{in}$. The increase in $V_{in}$ reduces the differential output of the amplification portion 290 and returns the system to stability.

The feedback signal from the feedback portion 291 is input to a positive input terminal of a comparator 255 of the readout portion 292.

Figure 3A:
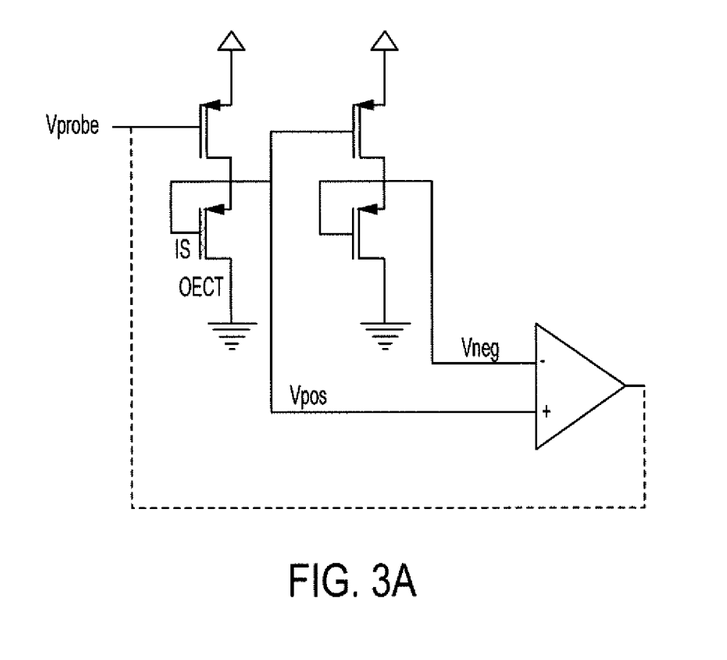
FIG. 3A shows the simulated circuit presented is that previously shown in FIG. 2C without the feedback loop.
Figure 3B:
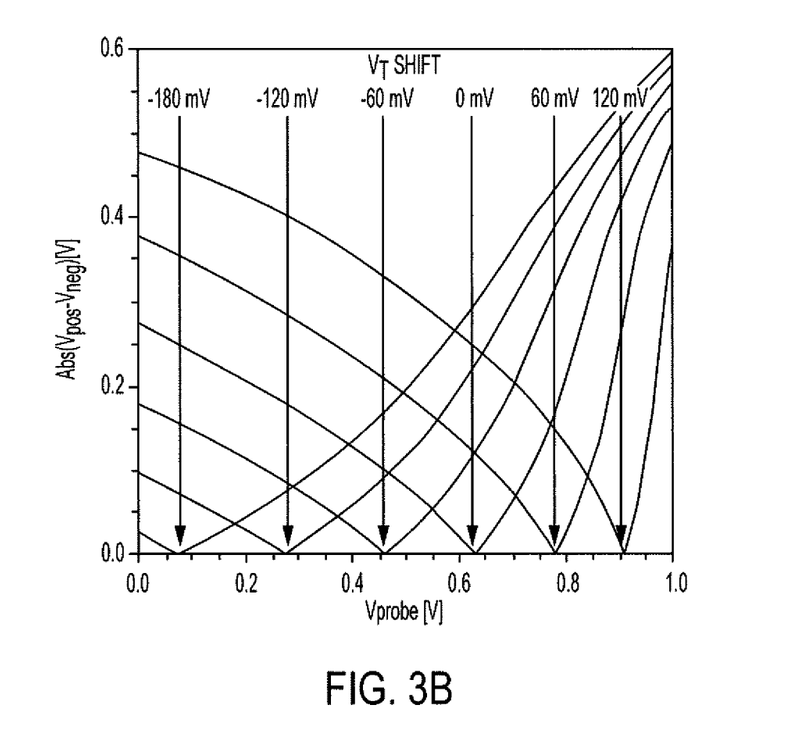
FIG. 3B shows Abs(Vpos−Vneg) for various threshold voltage shifts in increments of 60 mV of the IS OECT, which is the depletion load OECT in the first inverter 260.

Amplification extends the responsivity of the system above the maximum of 60 mV/decade of ion concentration for a purely capacitive device. Increasing the responsivity reduces the necessary bitprecision for ADCs, which reduces cost, lowers power consumption, and opens up the possibility of using other chips with different functionalities. FIG. 3A shows the simulated circuit presented is that previously shown in FIG. 2C without the feedback loop. The input Vprobe, is the same node that is read at the output of the full system in FIG. 2C. The circuit would stabilize at Vpos–Vneg=0 with the previously shown feedback implementation. FIG. 3B shows Abs(Vpos–Vneg) for various threshold voltage shifts in increments of 60 mV of the IS OECT, which is the depletion load OECT in the first inverter 260. This increment value corresponds to the maximum change in signal from an IS membrane per decade change in analyte concentration. A positive shift in the threshold voltage induced by changes in ion analyte concentration cause Vpos>Vneg for an unchanged Vprobe, necessitating a higher Vprobe to stabilize the output of the comparator 250 op amp (Vpos=Vneg) for the feedback loop.

Figure 3C:
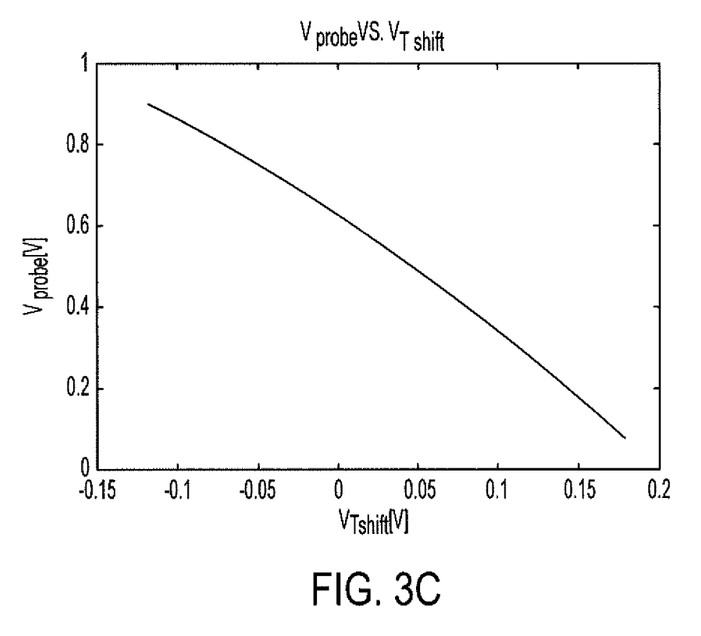
FIG. 3C shows the steady-state bias point of Vprobe with the feedback configuration of FIG. 2C as a function of threshold shift of the ion-selective OECT.
Figure 3D:
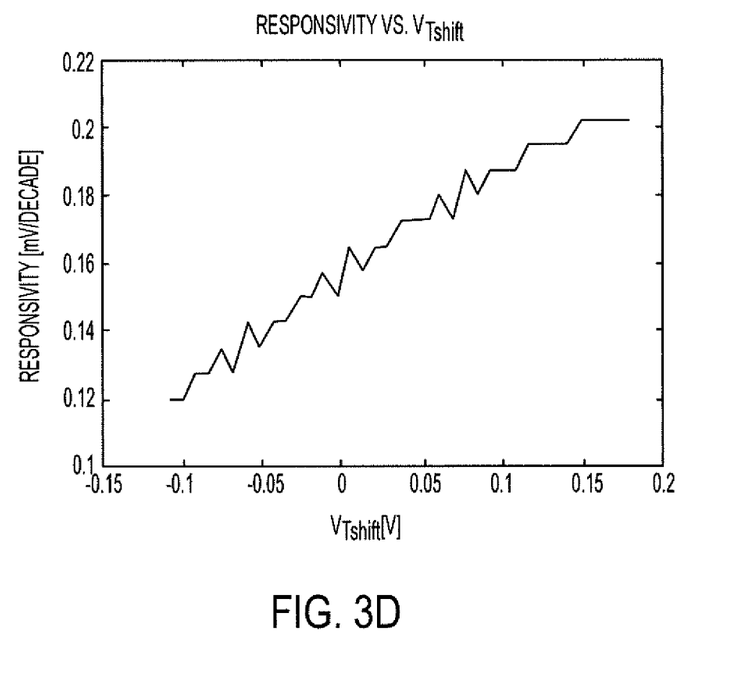
FIG. 3D shows responsivity vs. voltage.

FIG. 3C shows the steady-state bias point of Vprobe with the feedback configuration of FIG. 2C as a function of threshold shift of the ion-selective OECT. The responsivity of the sensor, measured in mV shift in Vprobe per decade change in analyte concentration, can range from 120 to 200 mV per decade. This responsivity is significantly higher than the 60 mV per decade of a typical ISM.

There are many possible variations of the current embodiment due to the nature of circuit design. Unique circuits can be designed depending on the power, resolution, or size constraints of the application. For instance, a well-designed inverter alone can offer a high amplification at a certain range of analyte concentration; however, the feedback implementation improves the dynamic range of this gain.

Alternatively, conventional electronic circuits may be used to amplify the signal of a capacitive ISM. However, this alternative has a drawback regarding the noise of the system. In contrast to this alternative, the negative feedback of the circuit in the systems and methods described herein minimizes the output noise of the system.

The systems and methods described herein utilize OECTs, a new class of devices with huge potential in transforming the landscape of biomedical engineering. These devices have been shown in literature to have very high transconductance in comparison to conventional transistors, which is necessary to convert a voltage signal from an ISM into an output current. The systems and methods described herein also utilize feedback to stabilize the output of the circuit.

Figure 4:
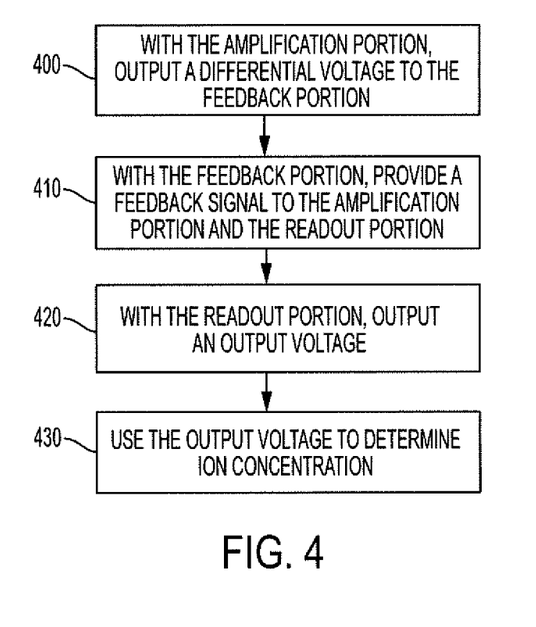
FIG. 4 is a flowchart of an embodiment of a method described herein.

In brief, in one aspect, FIG. 4 shows a flowchart of an embodiment. In step 400, with the amplification portion, differential voltage is output to the feedback portion. In step 410, with the feedback portion, a feedback signal is provided to the amplification portion and the readout portion. In step 420, with the readout portion, an output voltage is output, which is used in step 430 to determine ion concentration.

It will be further appreciated that the techniques disclosed herein may be embodied by a non-transitory storage medium storing instructions readable and executable by an electronic data processing device to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A device for measuring ion concentration in an analyte solution, comprising:
   an amplification portion comprising a first inverter and a second inverter, the first inverter comprising an ion sensing organic electrochemical transistor (OECT);
   a feedback portion configured to:
   receive a voltage input from the OECT; and
   provide a feedback signal to the first inverter and a readout portion.

2. The device of claim 1, wherein:
   the first inverter further comprises a non-sensing OECT comprising an encapsulant; and
   the second inverter comprises two non-sensing OECTs including encapsulants.

3. The device of claim 1, wherein the feedback portion comprises a comparator, a resistor, and a capacitor.

4. The device of claim 3, wherein the comparator is configured to:
   receive the voltage input from the OECT at a positive input terminal of the comparator; and
   output a feedback voltage to the capacitor and the resistor.

5. The device of claim 4, wherein:
   the capacitor is connected to a negative input terminal of the comparator; and
   the resistor is connected to the first inverter and the readout portion.

6. The device of claim 5, wherein:
   the resistor has a resistance of approximately 10 MΩ; and
   the capacitor has a capacitance of approximately 100 nF.

7. The device of claim 4, wherein the negative input terminal of the comparator is further connected to the second inverter.

8. The device of claim 1, wherein the readout portion is configured to:
   receive the feedback signal at a positive input terminal of a comparator; and
   output an output voltage to a negative input terminal of the comparator.

9. A device for measuring ion concentration in an analyte solution, comprising:
   an amplification portion comprising a first inverter and a second inverter, the first inverter comprising an ion sensing organic electrochemical transistor (OECT);
   a feedback portion configured to:
   receive a differential voltage signal from the amplification portion; and
   provide a feedback signal to the first inverter and a readout portion.

10. The device of claim 9, wherein:
    the first inverter further comprises a non-sensing OECT comprising an encapsulant; and
    the second inverter comprises two non-sensing OECTs including encapsulants.

11. The device of claim 9, wherein the feedback portion comprises a comparator, a resistor, and a capacitor.

12. The device of claim 11, wherein the comparator is configured to:
    receive the differential voltage from the amplification portion; and
    output a feedback voltage to the capacitor and the resistor.

13. The device of claim 12, wherein:
    the capacitor is connected to a negative input terminal of the comparator; and
    the resistor is connected to the first inverter and the readout portion.

14. The device of claim 13, wherein the negative input terminal of the comparator is further connected to the second inverter.

15. The device of claim 9, wherein:
    the first inverter further comprises a non-sensing OECT comprising an encapsulant encapsulating a reference solution; and
    the second inverter comprises two non-sensing OECTs including encapsulants encapsulating the reference solution.

16. A method of measuring ion concentration in an analyte solution, comprising:
    with an amplification portion comprising an ion sensing organic electrochemical transistor (OECT), outputting a differential voltage to a feedback portion; and
    with the feedback portion, providing a feedback signal to the amplification portion and a readout portion.

* * * * *